US007873437B2

(12) United States Patent
Aldred et al.

(10) Patent No.: US 7,873,437 B2
(45) Date of Patent: Jan. 18, 2011

(54) AUTONOMOUS MACHINE

(75) Inventors: Michael David Aldred, Wiltshire (GB);
Alexander Philip Bommer, Bristol (GB)

(73) Assignee: Dyson Technology Limited, Wiltshire (GB)

( * ) Notice: Subject to any disclaimer, the term of this patent is extended or adjusted under 35 U.S.C. 154(b) by 632 days.

(21) Appl. No.: 10/543,758

(22) PCT Filed: Feb. 13, 2004

(86) PCT No.: PCT/GB2004/000604

§ 371 (c)(1),
(2), (4) Date: Jul. 28, 2005

(87) PCT Pub. No.: WO2004/072752

PCT Pub. Date: Aug. 26, 2004

(65) Prior Publication Data

US 2006/0161318 A1 Jul. 20, 2006

(30) Foreign Application Priority Data

Feb. 14, 2003 (GB) ................................. 0303368.5

(51) Int. Cl.
G05B 19/18 (2006.01)
G05B 19/04 (2006.01)
(52) U.S. Cl. .................. 700/253; 700/245; 700/246; 700/250; 700/255
(58) Field of Classification Search .................. 701/23, 701/301; 340/435; 700/245, 250
See application file for complete search history.

(56) References Cited

U.S. PATENT DOCUMENTS

| 2,264,746 | A |   | 12/1941 | Ellwood |
| 4,962,453 | A | * | 10/1990 | Pong et al. ..................... 701/23 |
| 5,032,775 | A |   | 7/1991  | Mizuno et al. |
| 5,284,522 | A | * | 2/1994  | Kobayashi et al. ............ 134/18 |
| 5,341,540 | A |   | 8/1994  | Soupert et al. |
| 5,440,216 | A | * | 8/1995  | Kim ............................ 318/587 |
| 5,528,888 | A |   | 6/1996  | Miyamoto et al. |
| 5,537,017 | A |   | 7/1996  | Feiten et al. |

(Continued)

FOREIGN PATENT DOCUMENTS

DE          100 64 836          6/2002

(Continued)

OTHER PUBLICATIONS

International Search Report dated Jun. 4, 2004.

(Continued)

*Primary Examiner*—Dalena Tran
*Assistant Examiner*—Bhavesh V Amin
(74) *Attorney, Agent, or Firm*—Morrison & Foerster LLP

(57) ABSTRACT

A control system is provided for navigating an autonomous machine around a working area in a manner that causes the machine to traverse substantially all of the free surface of the working area. The control system is arranged to cause the machine to follow a boundary of the working area and to perform a plurality of movements, each movement comprising the machine travelling away from the boundary of the working area, at an angle to the boundary, and returning again to the boundary. The machine moves along the boundary of the working area between each movement and repeats the movements as the machine follows substantially the entire boundary of the working area.

23 Claims, 14 Drawing Sheets

U.S. PATENT DOCUMENTS

| | | | |
|---|---|---|---|
| 5,696,675 A * | 12/1997 | Nakamura et al. | 701/50 |
| 5,703,297 A | 12/1997 | Bauer | |
| 5,815,880 A | 10/1998 | Nakanishi | |
| 5,841,259 A | 11/1998 | Kim et al. | |
| 5,867,800 A * | 2/1999 | Leif | 701/23 |
| 6,496,755 B2 | 12/2002 | Wallach et al. | |
| 6,574,536 B1 * | 6/2003 | Kawagoe et al. | 701/23 |
| 6,615,108 B1 | 9/2003 | Peless et al. | |
| 7,054,716 B2 | 5/2006 | McKee et al. | |
| 7,173,391 B2 | 2/2007 | Jones et al. | |
| 7,320,149 B1 | 1/2008 | Huffman et al. | |
| 7,349,759 B2 | 3/2008 | Peless et al. | |
| 7,388,343 B2 | 6/2008 | Jones et al. | |
| 2004/0093650 A1 * | 5/2004 | Martins et al. | 901/1 |
| 2004/0207355 A1 | 10/2004 | Jones et al. | |
| 2006/0150361 A1 | 7/2006 | Aldred et al. | |
| 2006/0229765 A1 | 10/2006 | Bommer et al. | |

FOREIGN PATENT DOCUMENTS

| | | |
|---|---|---|
| EP | 0562559 A1 | 3/1993 |
| EP | 1003088 A1 | 10/1999 |
| GB | 1 252 134 | 11/1971 |
| GB | 0126499.3 | 11/2001 |
| JP | 62-120510 | 6/1987 |
| WO | WO-00/38025 A1 | 6/2000 |
| WO | WO-00/38029 A1 | 6/2000 |

OTHER PUBLICATIONS

GB Search Report dated Jul. 23, 2003.

Khairolomour, Rotary encoder mates with digital potentiometer, 2003, Internet, pp. 1-2.

Aldred, Michael David. U.S. Office Action, mailed Oct. 28, 2008, directed at U.S. Appl. No. 10/543,756; 14 pages.

Aldred, Michael David. U.S. Office Action, mailed May 19, 2009, directed to U.S. Appl. No. 10/543,756; 11 pages.

Bommer, Alexander Philip. U.S. Office Action, mailed Aug. 19, 2008, directed at U.S. Appl. No. 10/545,430; 9 pages.

Bommer, Alexander Philip. U.S. Office Action, mailed Mar. 9, 2009, directed at U.S. Appl. No. 10/545,430; 10 pages.

International Search Report mailed Jun. 4, 2004, directed at International Application No. PCT/GB2004/000587; 3 pages.

International Search Report mailed Jun. 24, 2004, directed at International Application No. PCT/GB2004/000601; 3 pages.

* cited by examiner

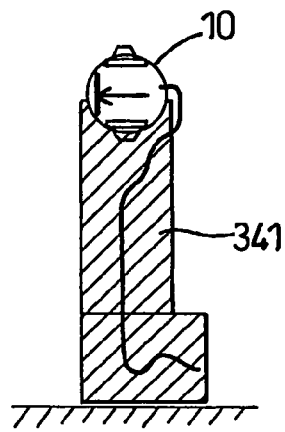 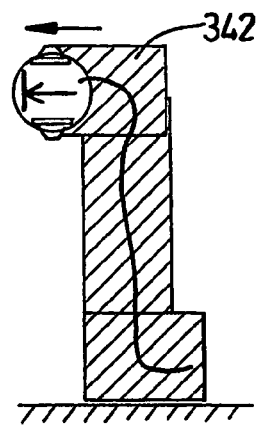 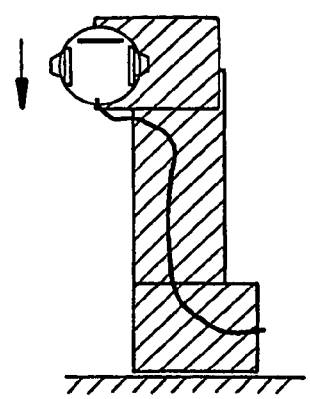
*Fig. 8A*   *Fig. 8B*   *Fig. 8C*
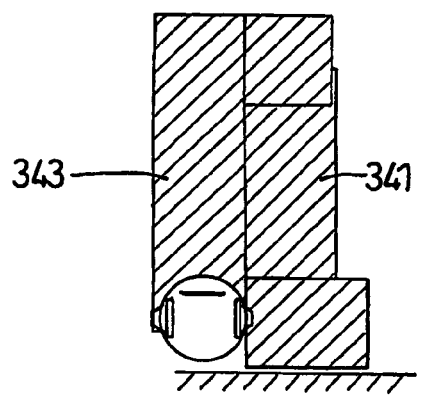 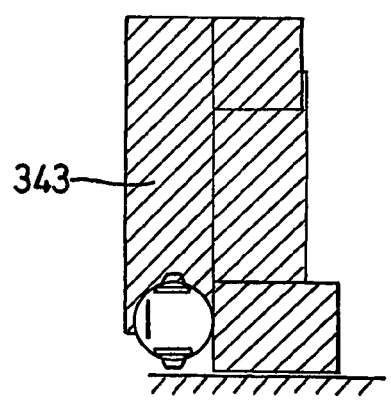
*Fig. 8D*   *Fig. 8E*

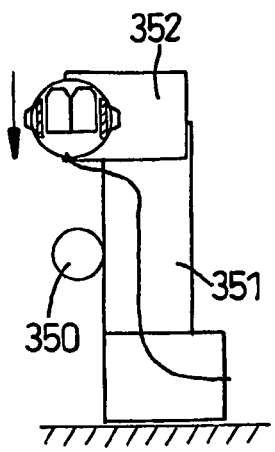
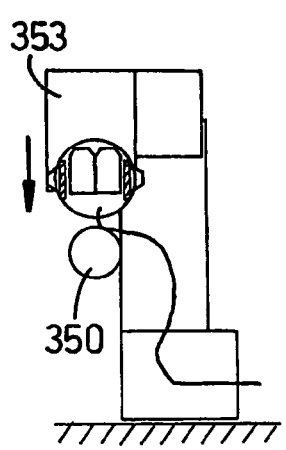
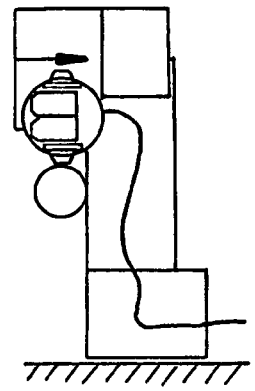
*Fig. 9A*  *Fig. 9B*  *Fig. 9C*
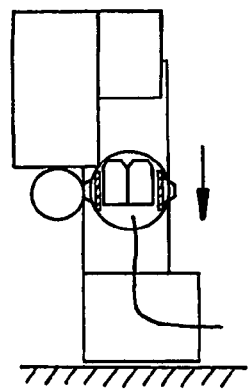
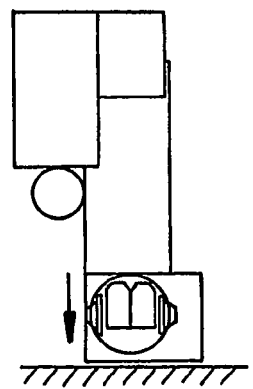
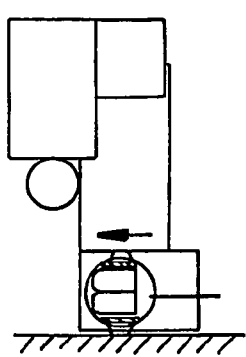
*Fig. 9D*  *Fig. 9E*  *Fig. 9F*

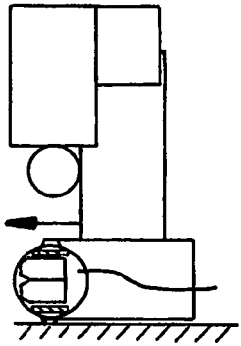 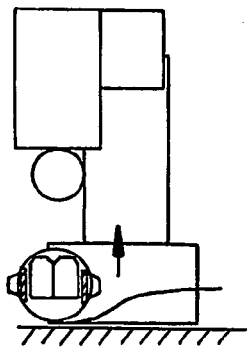 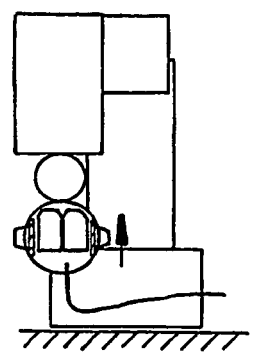
*Fig. 9G*   *Fig. 9H*   *Fig. 9I*
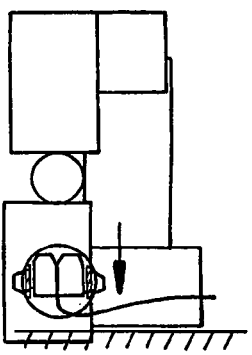 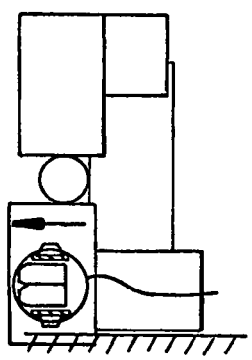 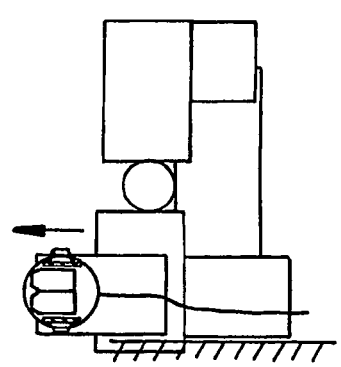
*Fig. 9J*   *Fig. 9K*   *Fig. 9L*

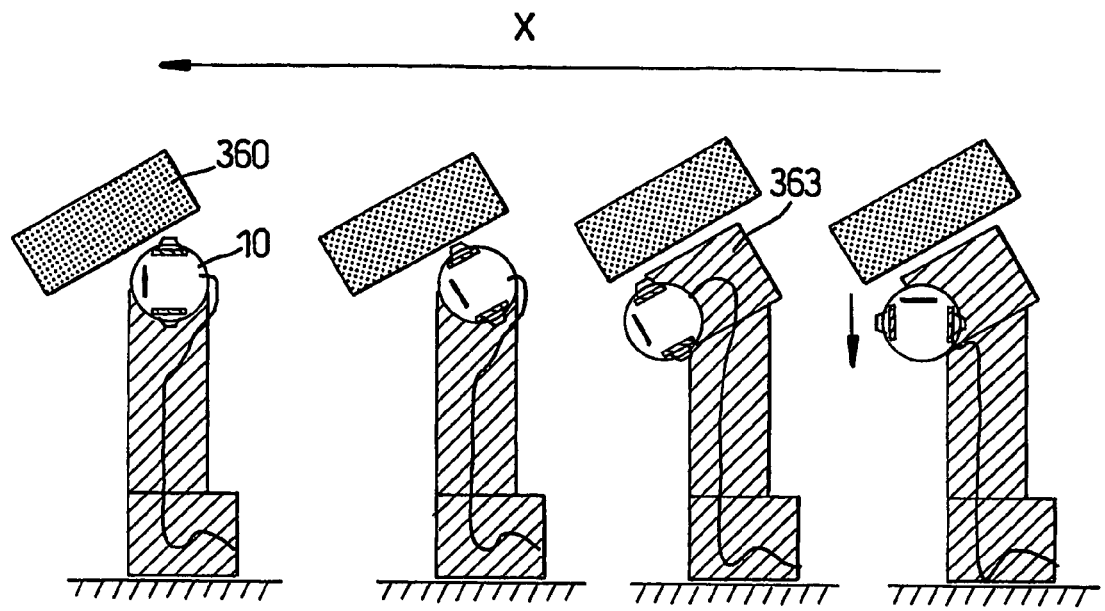
*Fig. 10A*  *Fig. 10B*  *Fig. 10C*  *Fig. 10D*
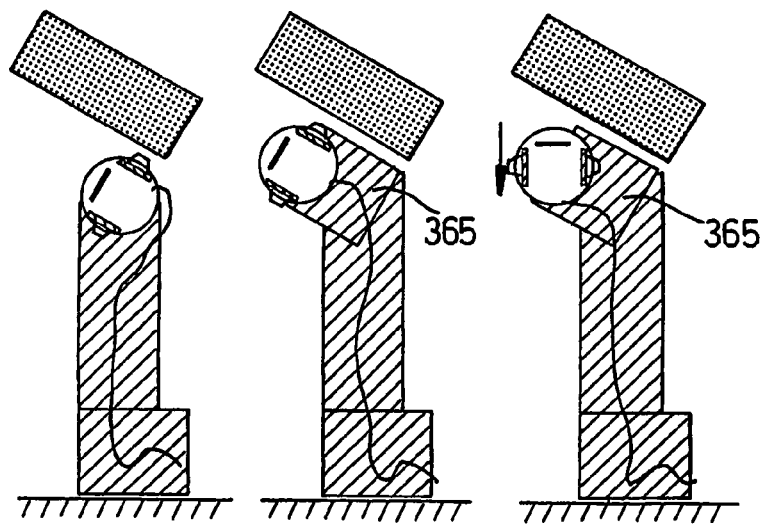
*Fig. 10E*  *Fig. 10F*  *Fig. 10G*

AUTONOMOUS MACHINE

FIELD OF THE INVENTION

This invention relates to an autonomous machine for performing a task which requires the machine to traverse substantially all of an area. The invention is particularly suitable for, but not limited to, an autonomous surface treating machine such as an autonomous vacuum cleaner, for cleaning a room of a building.

BACKGROUND OF THE INVENTION

There have been various proposals to provide autonomous or robotic machines for performing duties such as cleaning or polishing a floor area, or for mowing grass. In their simplest form, the machine requires a training phase during which the machine is manually led around the area in which it is to work. Following this training phase, the machine will then perform the required work as it follows the path which it stored in its memory during the training phase. Other machines may simply follow a predetermined route which is marked by means such as a cable which is buried beneath the working area. Machines of this type have the disadvantage of requiring supervision or a specially prepared working area.

Other autonomous machines are supplied with a map of the working area, the machine using this map to plan a route around the working area.

There have also been proposals for autonomous machines which are capable of exploring the environment in which they are placed without human supervision, and without advance knowledge (e.g. a map) of the layout of the environment. The machine may explore the environment during a learning phase and will subsequently use this information during a working phase, or the machine may begin working in the area immediately. An autonomous machine shown in WO 00/38025 initially travels around the perimeter of an area, recognises when it has completed a single lap of the area, and then steps inwardly after that and subsequent laps of the room so as to cover the area in a spiral-like pattern. Autonomous machines are also known to build a map of the working area using the information they acquire during the learning phase. Autonomous machines of this type are particularly attractive to users as they can be left to work with minimal human supervision.

Autonomous machines of this kind can cope very well with simple working areas, e.g. rooms with a rectangular shape, but they can often run into difficulties with more realistic working areas, such as those areas with an irregular shape or areas with obstacles placed at various positions within them.

It is also known to provide autonomous machines which derive their power from a mains power supply and which carry a reel of cable which is dispensed as the machine moves around the area. U.S. Pat. No. 4,962,453 shows an example of this kind of machine, which covers a working area by a complex series of fan-shaped coverage patterns.

SUMMARY OF THE INVENTION

The present invention seeks to provide an autonomous machine of the kind which performs a task which requires it to traverse substantially all of an area, where the machine is better able to cope with irregular working areas.

Accordingly, a first aspect of the present invention provides an autonomous machine that includes a control system for navigating the autonomous machine around a working area in a manner that causes the machine to traverse substantially all of the free surface of the working area. The control system is configured to cause the machine to follow a boundary of the working area and to perform a plurality of movements, in which each movement involves the machine travelling outwardly from the boundary of the working area, at an angle to the boundary, and returning again to the boundary. The machine moves along the boundary of the working area between each movement and repeats the movements as it follows substantially the entire boundary of the working area.

The invention has been found to work particularly well in working areas which have an irregular shape and/or working areas which have obstacles placed within them. All, or substantially all, of the working area is traversed by the machine on most occasions, which gives improved user satisfaction.

The invention is particularly suitable for use with an autonomous machine which derives its power from an external supply via a cable, since the control system both minimises the amount of cable which is dispensed on the surface of the area at any time and minimises the number of times the machine needs to cross an area where cable has previously been laid. It will be appreciated that the method performed by the control system is also suitable for use with machines which carry their own power supply, such as battery-powered machines.

The boundary can take many forms. In a room of a building, the boundary will be the walls of the room and the boundaries of objects placed within the room such as items of furniture. In an outdoor area, the boundary may be a pre-existing barrier such as a fence or wall or it may be any form of barrier which is positioned especially for use with the autonomous machine.

The navigation system can be implemented entirely in hardware, in software running on a processor, or a combination of these. Accordingly, a further aspect of the present invention provides software for operating the cleaning machine in the manner described herein. The software is conveniently stored on a machine-readable medium such as a memory device.

The autonomous machine can take many forms: it can be a floor treating machine such as a vacuum cleaner or floor polisher, a lawn mower or a robotic machine which performs some other function. Alternatively, it could be a general purpose robotic vehicle which is capable of carrying or towing a work implement chosen by a user.

BRIEF DESCRIPTION OF THE DRAWINGS

Embodiments of the present invention will now be described, by way of example only, with reference to the accompanying drawings, in which:

FIGS. 8A to 8E (collectively "FIG. 8") illustrate an alternative movement carried out by the machine of FIG. 1 using the navigation method of FIG. 4;

FIGS. 9A to 9L (collectively "FIG. 9") illustrate an alternative movement carried out by the machine of FIG. 1 using the navigation method of FIG. 4 during which an obstacle is encountered;

FIGS. 10A to 10G (collectively "FIG. 10") illustrate movements of the machine of FIG. 1 when obstacles which lie at an angle to the boundary of the working area are encountered;

DETAILED DESCRIPTION OF THE INVENTION

Figure 1:
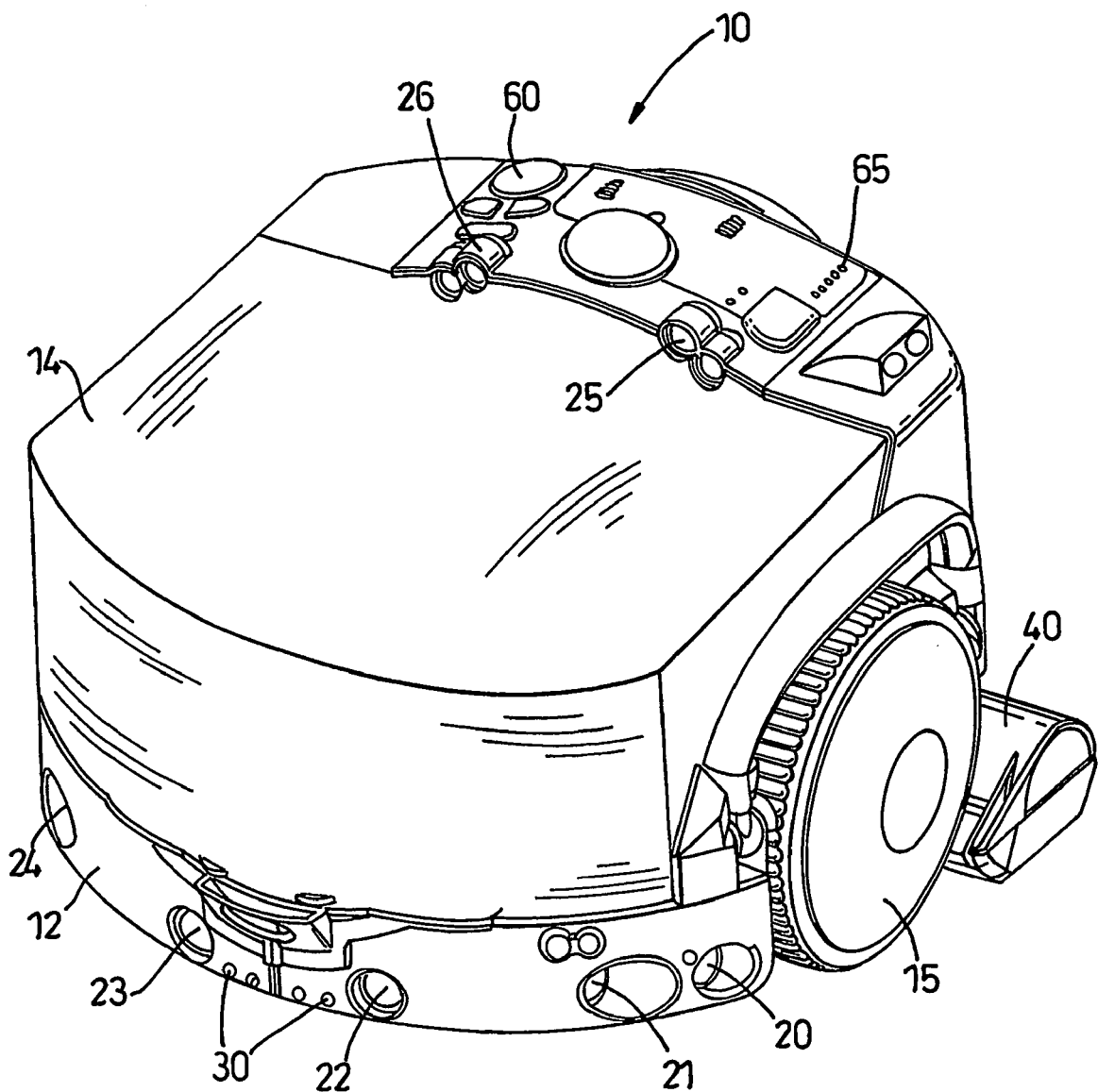
FIG. 1 shows an autonomous machine in the form of a vacuum cleaner.
Figure 2:
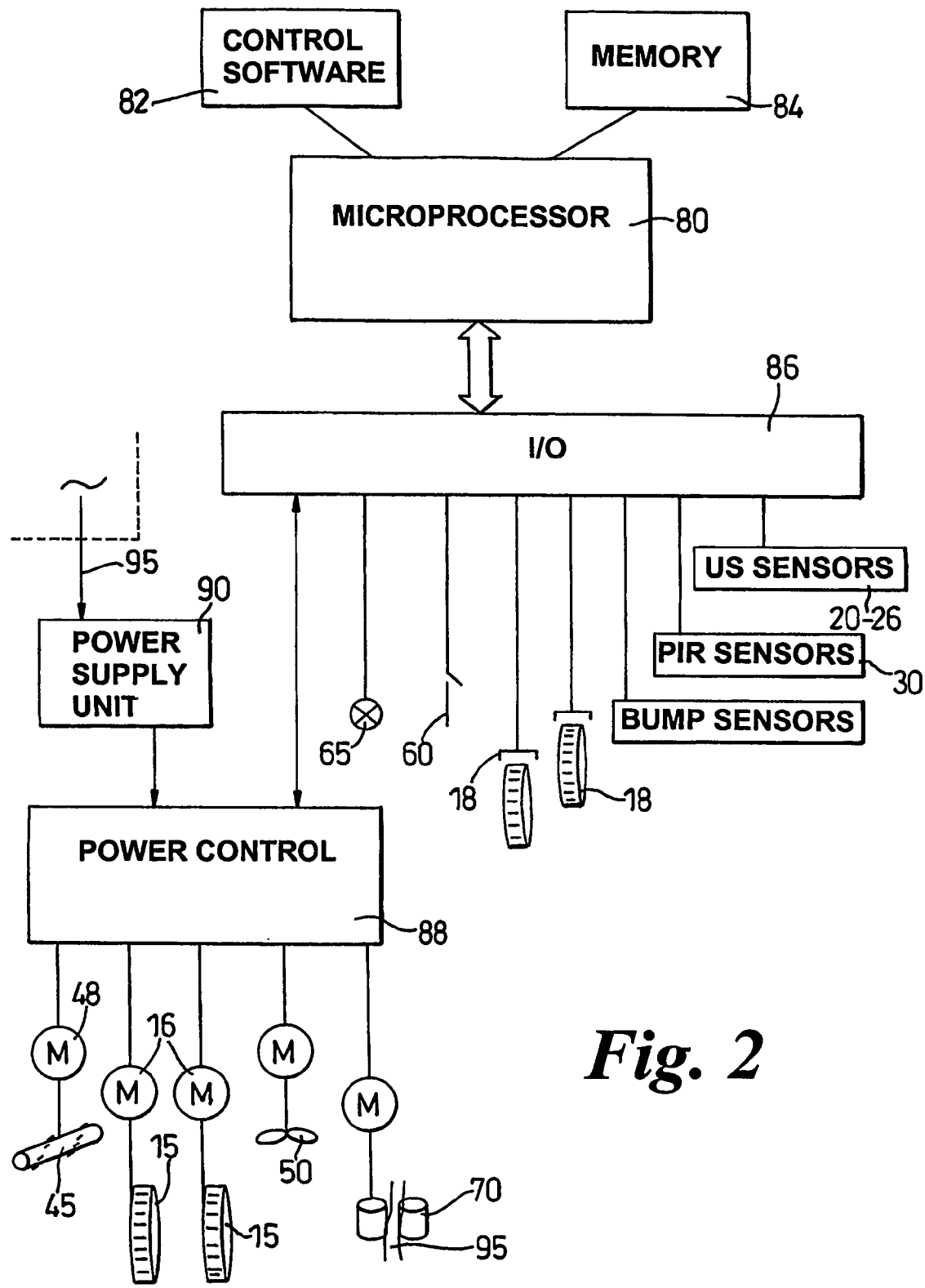
FIG. 2 shows the electrical systems of the machine of FIG. 1.

FIG. 1 of the drawings shows a robotic, or autonomous, floor cleaning machine in the form of a robotic vacuum cleaner 10. FIG. 2 shows the electrical systems incorporated into the vacuum cleaner 10.

The machine comprises a main body or supporting chassis 12, two driven wheels 15, a cleaner head 40, a user interface with buttons 60 and indicator lamps 65 and various sensors 20-26, 30 for sensing the presence of objects around the machine. Also mounted on the chassis 12 is apparatus 14 for separating dirt, dust and debris from an incoming airflow and for collecting the separated material, a reel for storing a length of power cable, and a system for dispensing and rewinding the power cable. The machine 10 is supported on the two driven wheels 15 and a castor wheel (not shown) at the rear of the machine. The driven wheels 15 are arranged at either end of a diameter of the chassis 12, the diameter lying perpendicular to the longitudinal axis of the cleaner 10. The driven wheels 15 are mounted independently of one another via support bearings (not shown) and each driven wheel 15 is connected directly to a traction motor 16 which is capable of driving the respective wheel 15 in either a forward direction or a reverse direction. A full range of maneuvers are possible by independently controlling each of the traction motors 16.

Mounted on the underside of the chassis 12 is a cleaner head 40 which includes a suction opening facing the surface on which the cleaner 10 is supported. A brush bar 45 is rotatably mounted in the suction opening and a motor 48 is mounted on the cleaner head 40 for driving the brush bar 45. It will be appreciated that the brush bar 45 could be omitted, if desired, so that the cleaner head 40 only has a suction opening and cleans by relying on suction alone. For other types of surface treating machine, the cleaner head 40 could be replaced by a polishing pad, wax dispenser, squeegee etc.

The chassis 12 of the machine 10 carries a plurality of sensors 20-26, 30 which are positioned on the chassis 12 such that the navigation system of the machine can sense obstacles in the path of the machine 10 and also the proximity of the machine to a wall or other boundary such as a piece of furniture. The sensors shown here comprise several ultrasonic sensors 20-26 which are capable of sensing the distance and angular position of walls and objects from the sensors, and several passive infra red (PIR) sensors 30 which can sense the presence of humans, animals and heat sources such as a fire. There are forward-facing sensors 22, 23, side-facing sensors 20, 21 and 24, 25, rear-facing sensors (not shown) and high-level sensors 26. It will be appreciated that the number of sensors, type of sensors and positioning of the sensors on the machine 10 can take many different forms. For example, infra red range-finding devices, also known as PSDs, may be used instead of, or in addition to, the ultrasonic sensors 20-26. In an alternative embodiment the machine may navigate by mechanically sensing the boundary of the working area and boundaries of obstacles placed within the area. One example of a mechanical sensor which could be used on a machine of this type is a "bump" sensor which detects movement of a moveable or resilient bumper when the machine encounters an obstacle. "Bump" sensors can be used in combination with the ultrasonic and PIR sensors described above.

One or both sides of the vehicle can also have an odometry wheel 18. This is a non-driven wheel which rotates as the machine moves along a surface. Each odometry wheel 18 has an encoder associated with it for monitoring the rotation of the odometry wheel 18. By examining the information received from each odometry wheel 18, the navigation system can determine both the distance travelled by the machine and any change in angular direction of the machine. It is preferred that the odometry wheel 18 is a non-driven wheel as this increases the accuracy of the information obtained from the wheel. However, in a simpler embodiment, the machine can derive odometry information directly from the driven wheels 15, by an encoder located on the wheel 15 or the motor 16 which drives the wheel 15.

The machine 10 also includes a motor 52 and fan 50 unit supported on the chassis 12 for drawing dirty air into the machine via the suction opening in the cleaner head 40.

The electrical systems for the machine, shown in detail in FIG. 2, will now be described. The navigation system comprises a microprocessor 80 which operates according to control software which is stored on a non-volatile memory 82, such as a ROM or FLASH ROM. Another memory 84 is used during normal operation of the machine to store data, such as odometry information and a map of the working area (if required), and other operating parameters. The navigation system receives inputs about the environment surrounding the machine from the sensor array 20-26, 30 (including ultrasonic, PIR and bump sensors) and inputs about movement of the machine from odometry wheel movement sensors 18. The navigation system also receives inputs from switches 60 on the user interface, such as starting, pause, stop or a selection of operating speed or standard of required cleanliness. The navigation system provides a plurality of output control signals including signals for driving the traction motors 16 of the wheels 15, a signal for operating the suction motor 52 which drives the suction fan 50 and a signal for operating the motor 48 which drives the brush bar 45. It also provides outputs from illuminating indicator lamps 65 on the user interface. Power is derived from a mains supply via a power cable. The cleaner carries a cable reel 95 with a length of cable (e.g. 20 m) which is sufficient to allow the machine to circumnavigate a typical room in which the machine will be used.

Figure 3A:
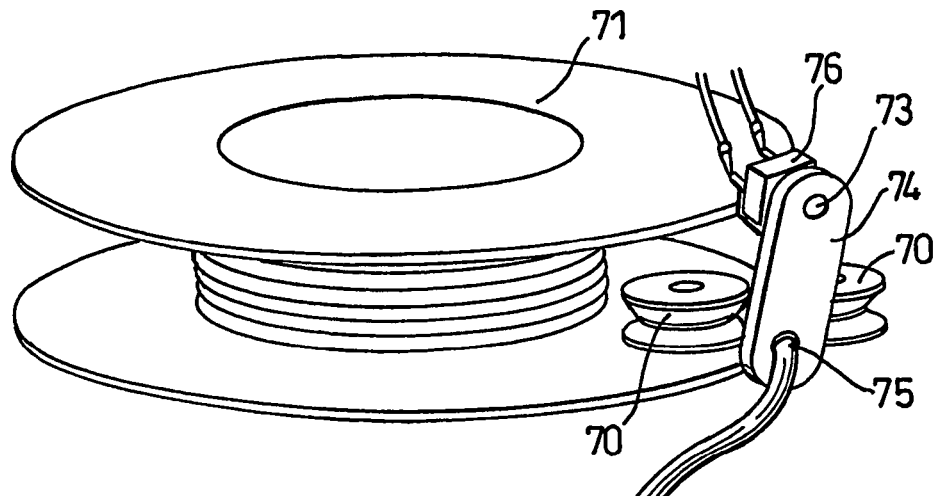
FIGS. 3A-3D (collectively "FIG. 3") show the power cable management system of the machine of FIGS. 1 and 2.
Figure 3B:
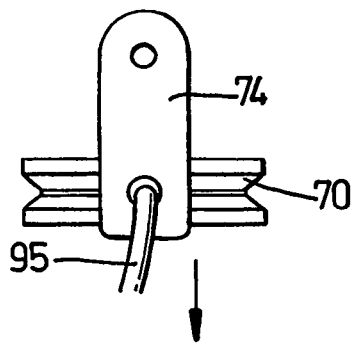
Figure 3C:
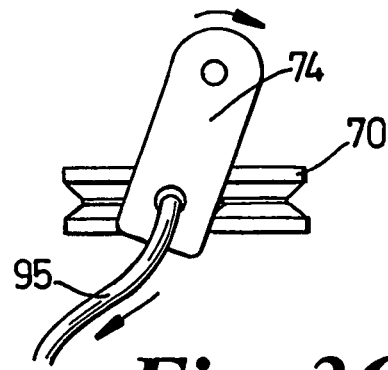
Figure 3D:
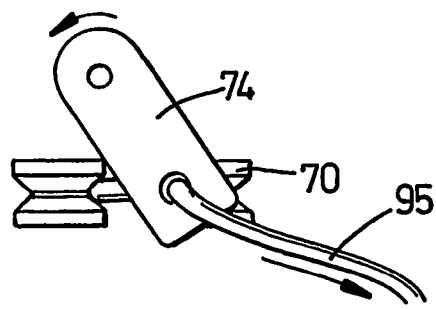

There are various ways of managing cable storage on the machine. FIG. 3 shows one preferred scheme. Power cable 95 is stored on a cable reel 71. The cable reel 71 is permanently biased, by a spring, towards the wound up state. Cable 95 is drawn from the reel 71 by a pair of pinch rollers 70, one of which is driven by a motor 72, under the control of the navigation system, to dispense cable from the reel 71, or to allow cable 95 to be rewound onto the reel 71, as the machine moves around a working area. After passing through the pinch rollers 70, the cable 95 passes through an opening 75 in the free end of a pendulum 74. The pendulum 74 is pivotable about a shaft 73, the pendulum 74 being movable in a vertical plane. Shaft 73 forms part of a rotary encoding device, such as a potentiometer, which can provide an output signal proportional to movement of the pendulum 74. As shown in FIGS. 3B to 3D, the pendulum 74 tracks the position of the cable 95 with respect to the cable reel 71. This allows the machine to detect the angle at which the cable 95 lies with respect to the machine. This is particularly useful when the machine is reversing along a path where cable 95 has been laid. The control system can detect the position of the cable, and the machine can be controlled to follow the path of the cable 95. This technique will hereafter be referred to as 'cable follow mode'.

It will be appreciated that if the machine is battery powered, then the chassis 12 carries one or more battery packs for supplying power to the machine, and the cable reel 71 and cable management system are not required.

Figure 4:
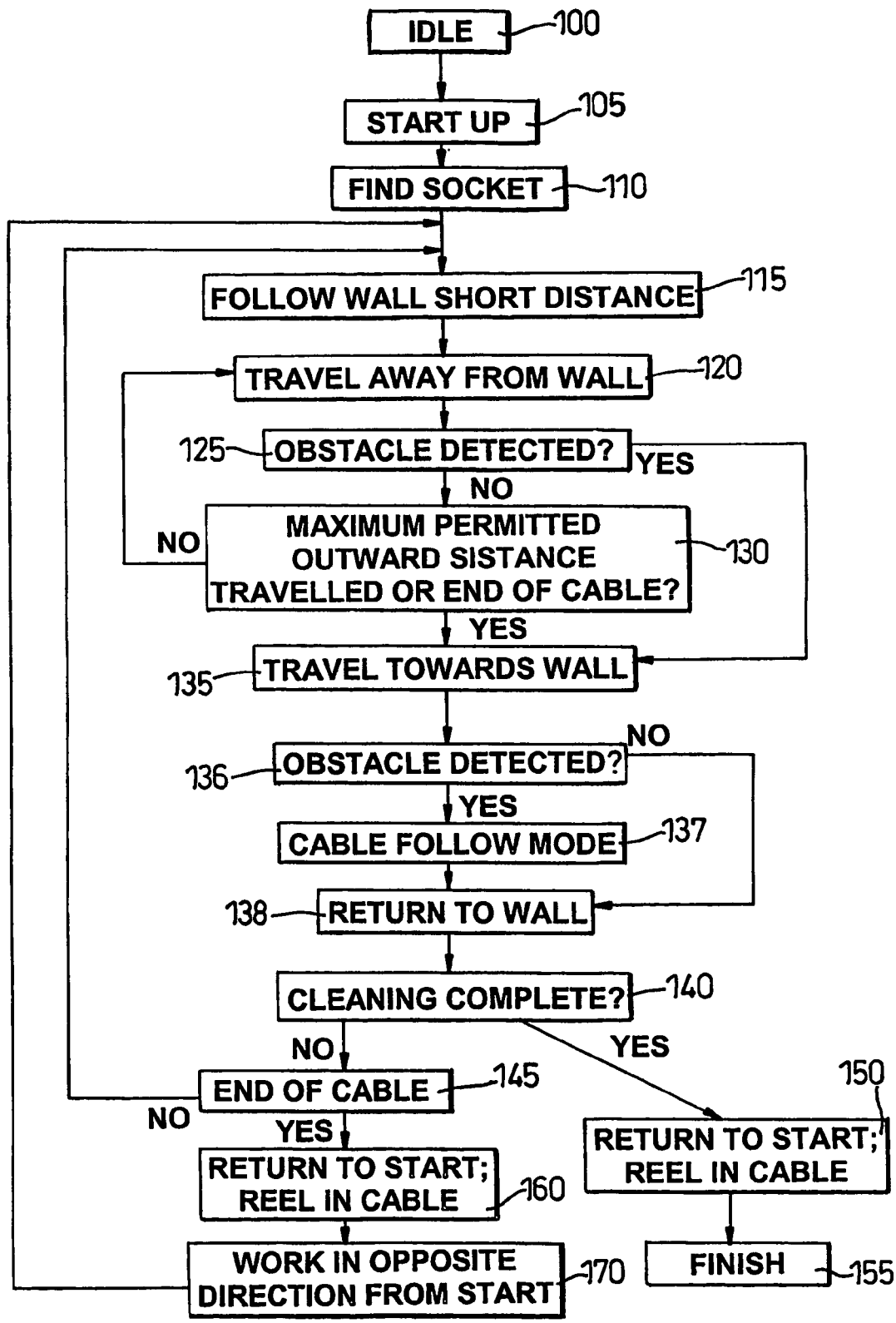
FIG. 4 is a flow chart of the navigation method used by the machine.

The operation of the machine will now be described with reference to FIGS. 4 to 9. FIG. 4 is a flow chart of the general process for navigating the machine around a working area.

FIGS. 5 to 9 show the machine 10 at work, in a room of a house. The boundary of the working area for the machine is defined by the walls of the room 301-304 and the edges of objects 305-308 placed within the room, such as articles of furniture (e.g. sofa, table, chair). These figures also show the set of paths 320 traversed by the machine.

The following description is based on a mains powered machine which requires a power cable 95 to connect the machine to a mains socket 310. It will be appreciated that, for a self powered machine, all references to laying and retrieving the power cable can be ignored.

The machine 10 is placed in the room by a user. Ideally, the machine is left near to a power socket 310 in the room, with the plug inserted into the socket 310 and a short length of power cable lying on the floor between the socket and the machine 10. Once the machine has been switched on, it begins a short routine to discover a starting or 'home' position in the room (step 110). The power socket 310 is a convenient home position for the mains powered machine. The 'home' position serves as a useful reference point for determining, inter alia, when the machine has travelled around the entire room. The machine determines the position of the power socket 310 by winding the cable 95 onto its internal cable reel 71 as it reverses. The machine can find the socket 310 by mechanically sensing that the cable 95 has been fully rewound, or by detecting a marker 98 placed on the cable 95, near to the plug. The machine then aligns its left hand side with the boundary of the area and starts the suction motor 52 and brush bar motor 48. It waits until the motors 48, 52 reach operating speed and then moves off. As the cleaner moves forwards (step 115) it dispenses power cable 95 from the cable reel so that the cable lies substantially along the path taken by the machine 10. Due to the potential for odometry errors, the cable 95 may be dispensed at a rate which is slightly higher than the rate of movement of the machine 10.

Figure 7A:
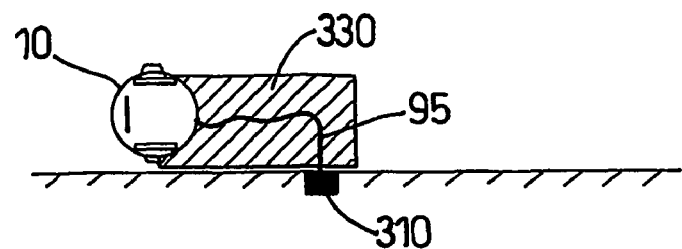
FIGS. 7A, 7B and 7C (collectively "FIG. 7") illustrate a movement carried out by the machine of FIG. 1 using the navigation method of FIG. 4.
Figure 7B:
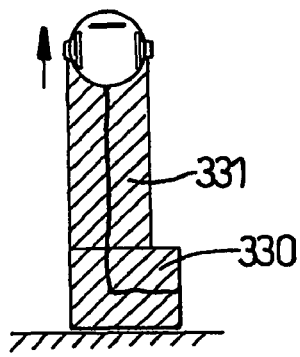
Figure 7C:
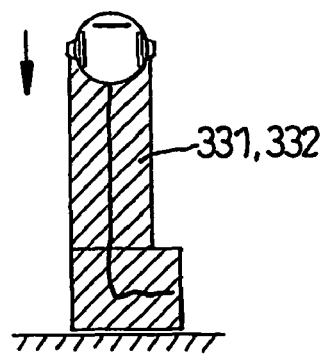

The machine then begins a series of maneuvers which in combination will be referred to as a 'spike'. The basic spike is shown in FIG. 7. The machine turns so that it is pointing away from the boundary (wall), inwards into the working area. It travels forwards on a path which is substantially perpendicular to the boundary (step 120). The machine derives information on the distance and direction of travel from the odometry wheel sensors 18. As the cleaner moves forwards, along path 331, it dispenses sufficient power cable 95 from the cable reel 71 so that the cable 95 lies slackly along path 331. During this movement, the machine continually monitors inputs from the sensor array 20-26,30 to sense the presence of any obstacles in its path. The machine continues to travel forwards until one of a number of conditions are met. Should the machine sense the presence of an obstacle (step 125) or the absence of a surface (e.g. a staircase), or if the machine senses that it has dispensed all of the power cable 95 from the reel 71, or if it senses some other fault condition, it will immediately stop. If none of these conditions are met, the machine will stop after a predetermined distance has been travelled from the boundary. This distance will depend on the type of working area where the vehicle is working. In a domestic environment we have found that a maximum distance of 2-3 m works well.

Once the machine has stopped, having met one or more of the conditions mentioned above, it reverses back towards the boundary following a similar path 332 (step 135, FIG. 4). The machine rewinds cable 95 during this return maneuver. For best cleaning performance, the suction motor 52 and brush bar motor 48 are operated during this return maneuver so as to treat the same area of floor twice. This replicates the kind of 'to and fro' cleaning action that a human user performs when they use a vacuum cleaner. As an alternative, during this return maneuver the suction motor 52 and brush bar motor 48 can be switched off. This would be a useful way of increasing battery life for a battery powered machine. During the return maneuver, the machine can navigate towards the boundary by using odometry information or it can follow the cable 95 which was laid on the floor during the outward trip, the process previously described as 'cable follow mode'. This outward trip into the working area and back again to the boundary constitutes the previously mentioned 'spike'.

As the length of the outward part of the spike increases, the likelihood that the machine will drift from the intended path also increases. Odometry errors, wheel slippage, changes of surface material and the direction of carpet pile are some factors which can cause the machine to drift from an intended path. In the unlikely event that the outward and return paths of the spike are spaced apart and an object lies between the paths, then there is a risk that the power cable can become wrapped around the object. In these circumstances, it is preferable for the machine to navigate back to the boundary in cable follow mode (steps 137, 138).

Once the machine has returned to the boundary, which it can sense from its sensor array and odometry information, it turns so that it is once again pointing in a clockwise direction, with its left-hand side aligned with the boundary. It moves forwards for a short distance which is sufficient to bring the machine next to the strip of the floor which has just been treated. The cleaner then turns so that it is again pointing away from the boundary, inwards into the working area. The machine then travels forwards at an angle which is substantially perpendicular to the boundary, as before. The machine continues as previously described, traversing a strip of the floor surface which is adjacent, or overlaps, the area previously treated.

Figure 5:
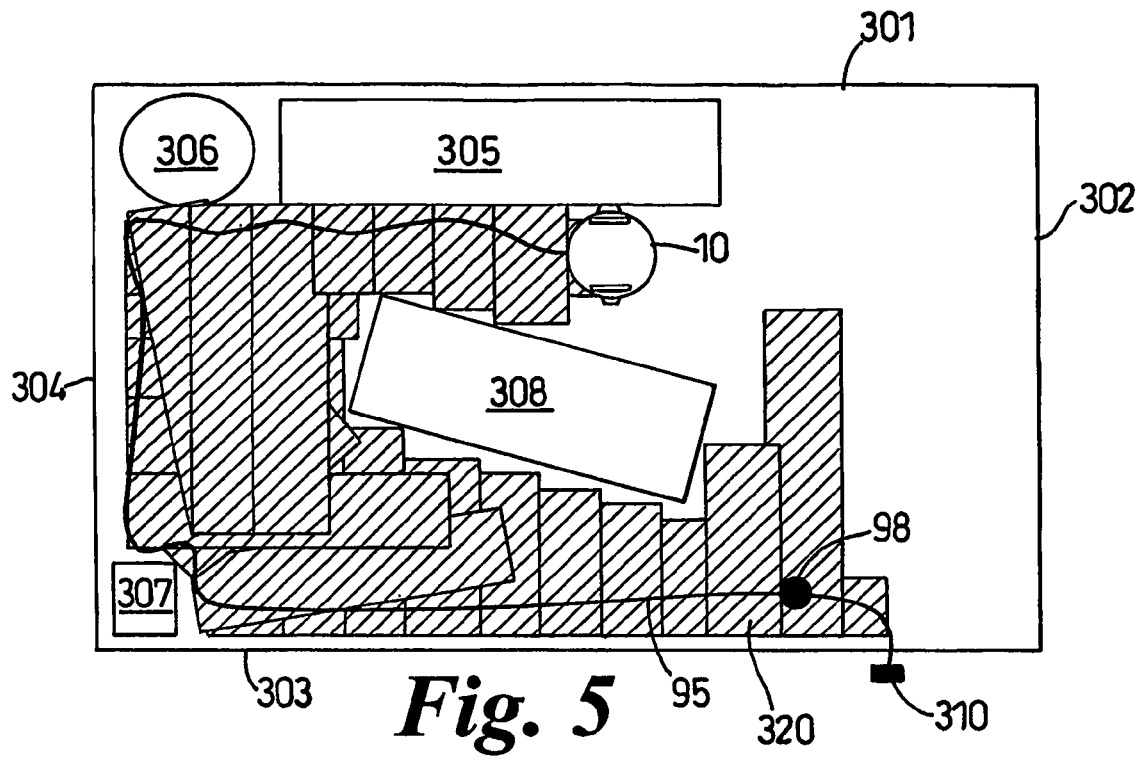
FIGS. 5 and 6 show the machine at work in a working area, following the navigation method of FIG. 4.
Figure 6:
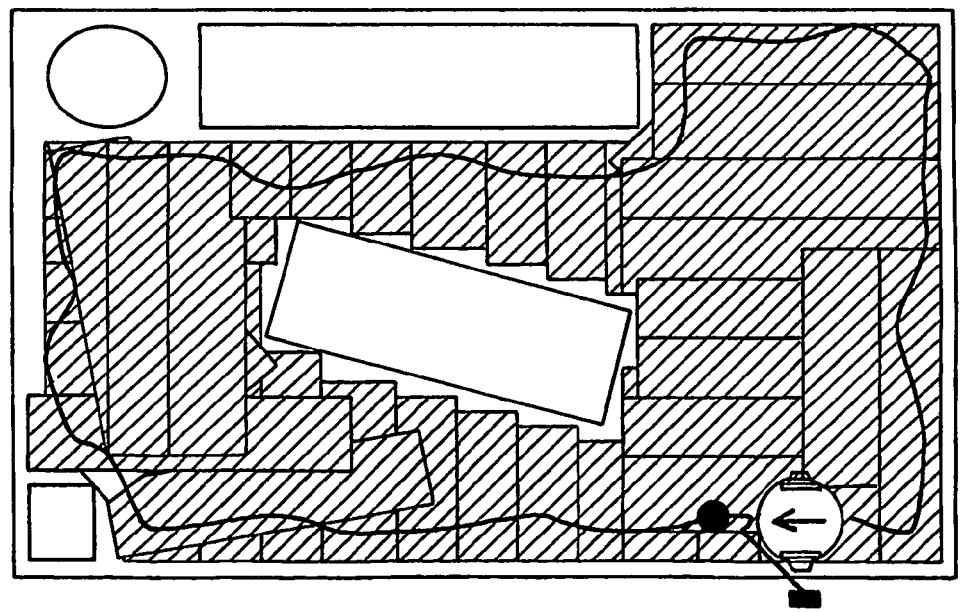

The machine repeats this sequence of steps so as to traverse a plurality of paths extending into the working area from the boundary, as can be seen in FIGS. 5 and 6. As the machine progresses around the boundary it can be seen that the spikes originating at different parts of the boundary can overlap one another. This helps to ensure that as much of the working area as possible is treated by the machine 10.

After completing each spike, the machine checks whether it has covered the entire working area (step 140). This check can be performed in various ways. In its simplest form, the machine can use an on-board sensor to sense whether it has returned to a starting position on the boundary. Preferably, a marker 98 is provided on the power cable 95 at a position adjacent the plug so that the machine can sense when it has returned to this position. The marker 98 can be a magnetic marker and the machine can be provided with a magnetic field sensor, such as a Hall-Effect sensor, for sensing the marker. In a more advanced machine, the machine generates a map of the working area and updates this map so as to record areas of floor visited by the machine. Thus, by using this map, the machine can determine when it has completely covered the working area. After each spike the machine also checks (step 145) to ensure that it has sufficient cable 95 remaining on the cable reel 71 to continue travelling around the boundary.

Step 145 requires the machine to have the capability to detect the amount of cable 95 remaining on the cable reel 71. This can be achieved by marking the cable 95 in a manner which indicates the quantity of remaining cable 95 and providing the control system with a sensor which can detect the markings. Alternatively, an encoder on the pinch roller 70 can feed the control system with an indication of the amount of cable 95 dispensed from the reel 71. This is advantageous because the same mechanism can be used to detect any jamming of the cable 95. In a simpler machine this step can be omitted entirely and the machine can simply stop when all of the cable 95 has been dispensed from the reel 71, wherever this may be in the room.

If the machine determines that it has completely covered the working area, it travels back to the starting position in the working area. The machine can follow the boundary of the working area, rewinding the cable 95 as it moves around the boundary. Alternatively, the machine can operate in cable follow mode, rewinding the cable 95 and following the path formed by the cable 95 on the surface of the working area. In the event that this brings the machine near to an obstacle, the machine can revert to a boundary following mode of operation until it is determined that the cable 95 leads away from the obstacle, whereupon the machine can once again operate in cable follow mode. The machine will eventually return to the starting point near to the power socket 310.

There are a number of possible variations to the basic method just described.

Firstly, it is possible to vary the spacing between each spike from the boundary. A spacing which brings the spikes next to one another with little or no overlap will obviously allow the machine to cover the entire working area in the shortest possible time, but it has the disadvantage that some areas may not be covered at all if the adjacent spikes are not parallel to one another over their entire length. Odometry errors, wheel slippage, changes of surface material and the direction of carpet pile are some factors which can cause the machine to drift from a true path. We prefer to overlap adjacent spikes by between 0 and 50%. Overlapping adjacent spikes has the advantage that a more thorough treatment of the surface is possible. It also reduces the chance that some parts of the surface are not treated at all.

In a second refinement of the basic method, the spike movement performed by the machine is modified so that the simple outward and return trip from the boundary is modified into an outward, step across and return trip. This is shown in FIG. 8. This movement has an advantage in that it covers the working area more quickly, although this has the associated disadvantage of treating each area of the surface covered by the spike only once instead of twice. Firstly, the machine turns to point outwardly from the boundary, perpendicular to the boundary. It then travels forwards, dispensing cable 95 as it moves forwards, along path 341. During this movement, the machine continually monitors inputs from the sensor array 20-26, 30 to sense the presence of any obstacles in its path. The machine continues to travel forwards until either the machine senses the presence of an obstacle or a predetermined distance has been travelled. The machine will then stop. At the end of the outward trip, the machine turns anticlockwise through 90° FIG. 8A) and then moves forwards for a short distance along path 342 (FIG. 8B). The machine then turns clockwise through 90° (FIG. 8C) and reverses along path 343, which is substantially parallel to the outward path 341 (FIG. 8D). The distance by which the machine steps across is sufficient to achieve any desired overlap. Finally, the machine turns anticlockwise to follow the boundary once again.

It is possible for the machine to run out of power cable 95 during the outward trip before either an obstacle has been sensed or the predetermined distance has been travelled. In this case, the machine will simply reverse along the path of the outward trip in a manner similar to that shown in FIG. 7 without attempting to step across. This is to avoid placing tension on the cable 95.

A consequence of the machine stepping across during the spike is that the machine could encounter one or more obstacles during its return trip to the boundary, since the machine will be travelling along a new path. This scenario is shown in the sequence of drawings which comprise FIG. 9. The path followed by the machine and shown in FIGS. 9A and 9B replicate that shown in FIGS. 8A to 8C and part of 8D. However, during the return trip, the machine senses the presence of an obstacle 350 between itself and the boundary. The machine rotates 90° anti-clockwise and reverses around the obstacle (FIG. 9C and 9D) until it reaches a position where the cable leads away from the obstacle. The machine then enters cable follow mode or uses odometry information until it reaches the wall following its earlier outward path (FIG. 9E). It then turns anti-clockwise to align its left hand side with the boundary (FIG. 9F), moves along the boundary by a standard step distance (FIG. 9G), and performs a simple spike by travelling outwards as far as the obstacle 350 and reversing back to the boundary (FIGS. 9H, 9I). Once this is completed, the machine turns anticlockwise to re-align its left hand side with the boundary (FIG. 9K) and steps across to commence a new spike (FIG. 9L).

In the methods shown in FIGS. 8 and 9 the machine 'steps across' (e.g. path 342 in FIG. 8) along a path which lies substantially parallel to the boundary of the working area. However, in realistic scenarios the machine is likely to encounter obstacles which have an edge which is set at an angle to the boundary of the working area. FIGS. 10A-10G show how the machine can cope with such obstacles. FIGS. 10A-10D show an obstacle which is inclined towards the boundary while FIGS. 10E-10G show an obstacle which is inclined away from the boundary. In FIG. 10A the machine spikes outwardly from the boundary of the working area, reaches an obstacle 360 and stops. It then turns in an anti-clockwise direction to align itself with the edge of the obstacle 360 which faces the boundary of the working area (FIG. 10B). The control system then determines the distance by which the machine needs to move along the new diagonal path 363 to achieve the required step across distance in the X direction, i.e. the direction parallel to the boundary of the working area. This is a simple trigonometric calculation. Once this distance has been travelled (FIG. 10C), the machine turns in a clockwise direction (FIG. 10D) and reverses towards the boundary, following a path which is substantially parallel to the outward path. In FIGS. 10E-10G the machine operates in a very similar manner, the difference being that the step across maneuver is along a path 365 which extends diagonally away from the boundary of the working area.

Figure 11:
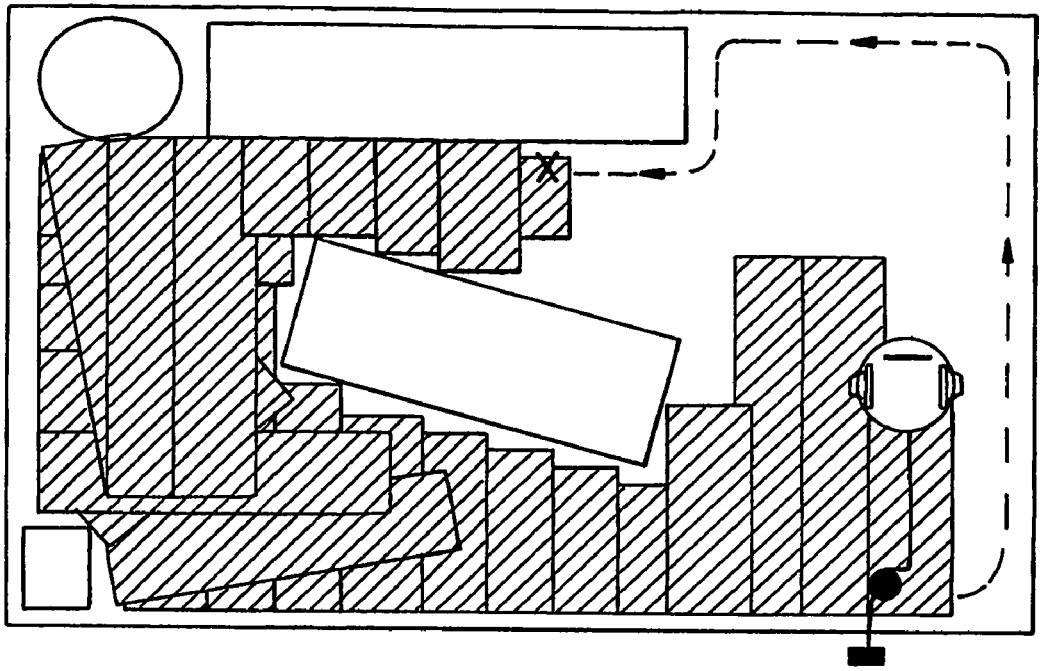
FIGS. 11 and 12 illustrate the ways in which the machine copes with large working areas.

In large working areas the machine may run out of cable before it has completely covered the working area. In this case, the machine proceeds to perform the same technique as has previously been described in the opposite direction from the starting point (step 170, FIG. 4). Thus, the cleaner follows the boundary in an anti-clockwise direction, aligning the right-hand side of the machine with the boundary of the area and performing a series of spikes outwardly from the boundary of the working area. FIG. 11 shows the same area as previously shown in FIG. 5. It is assumed that during the initial clockwise trip around the area, the cable was fully dispensed at point X. The machine has returned to the start point at the socket 310 and has begun travelling anti-clockwise around the boundary. The machine begins 'spiking' as soon as it returns to the start position. It will be appreciated that the spike movements performed by the machine as it travels anti-clockwise around the boundary are mirror images of the spike movements illustrated in FIGS. 7 to 10. The machine will continue in this manner until either the cable 95 is again fully dispensed or the navigation system detects that point X has been reached or passed.

Figure 12:
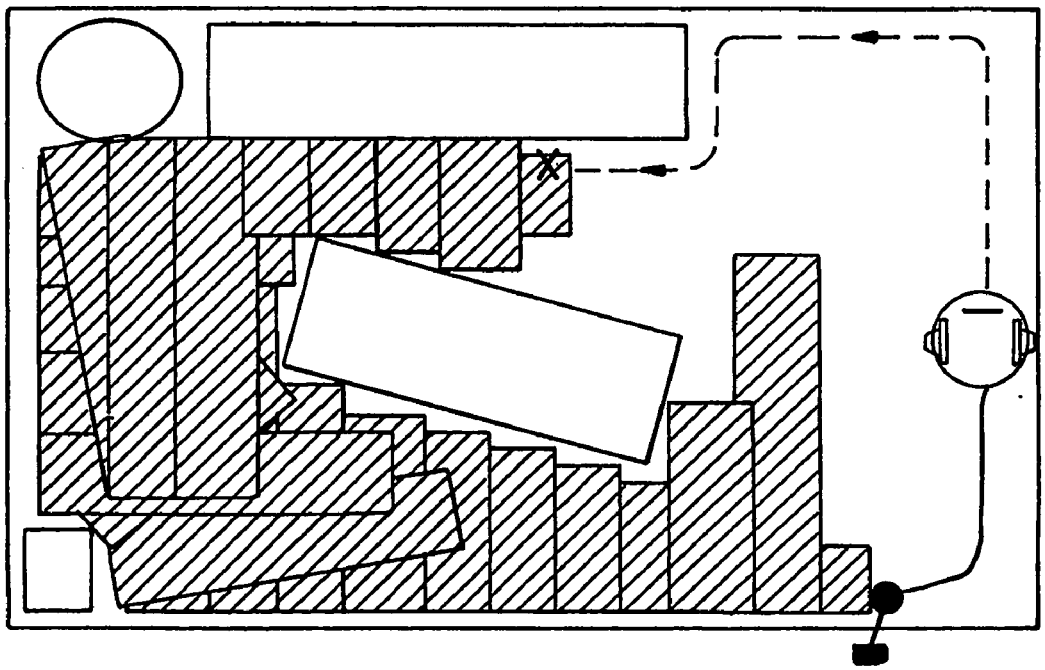

FIG. 12 shows an alternative scheme in which the machine, once it has returned to the start point at the socket 310, begins to travel around the boundary in the anti-clockwise direction. However, instead of immediately beginning to spike into the area, it simply travels around the boundary, dispensing cable, until the navigation system detects that point X has been reached or passed. The reason for this difference is because it may be easier for the machine to detect when it reaches point X if the machine travels there directly as there will then be fewer accumulated odometry errors.

For the machine accurately to detect when it has returned to a point where cleaning finished previously (such as point X in FIG. 11), it requires some form of mapping function. The machine needs to have the capability to map the working area and record where it has visited in the working area. The map can be constructed using odometry information which is acquired from the odometry wheels 18 and/or information about features of the working area which is acquired from the object detection sensors 20-26, 30 in a manner which is known in the art. The machine can then use the map to determine when it has returned to a point on the boundary which it previously reached via a journey in the opposite direction around the boundary. It is preferable to allow a good overlap region, as accumulated odometry errors can cause some error between the actual position of the machine, and the position of the machine as determined by the map.

If the machine lacks any form of mapping function, then it can simply continue to work in the opposite direction around the working area until the cable has all been dispensed. This can result in a considerable region where the surface is treated twice.

The above method describes the machine following an anti-clockwise path around an area. The machine may equally take a clockwise path around the area during its initial lap of the boundary of the area.

The navigation method can be applied to a machine which does not rely on a power cable to supply the machine with power. For a non-cabled machine the navigation method can be somewhat simplified. Firstly, the machine need only travel once in one direction around the entire boundary of the working area since the machine does not need to rewind the cable, and it is not limited to a maximum length of unwound cable. This can simplify the requirements of the sensor array of the machine, since only one side of the machine (the left-hand side for anti-clockwise operation around a working area) requires sensors for sensing distance from the boundary. As the machine will not be able to operate in cable follow mode, it will need to rely more heavily on odometry information and the sensor array during the return path of the spike movement, and during the return to the starting position.

As described above, one of the problems with an autonomous machine which lacks any advance knowledge of its working area is how the machine determines when it has completed a trip around the entire perimeter of the area and returned to a starting point. The cable-based machine described above can conveniently use the power socket as a starting point.

A non-cable based machine requires an alternative way of recognizing when it has returned to a previously visited location in a working area. Our pending patent application GB 0126499.3 describes one such method. The machine stores a record of the path travelled and repeatedly attempts to match the latest portion of the path with all previously stored portions of the path until a match is found. Other ways of determining when the machine returns to a starting point include positioning a beacon or marker on the boundary and providing the machine with a sensor which is capable of recognizing the beacon or marker. The beacon can be of the active or passive type, i.e. it can include a power source so that it can continuously or periodically emit a signal, or it can respond to an interrogatory signal transmitted by the machine. Suitable beacons are described in WO00/38029.

The method which has been described should ensure good coverage of the working area. In its simplest form, the machine performs a 'spike' into the working area at an angle which is substantially 90° to the angle of the portion of the boundary from which the spike commences. A further enhancement, which will now be described with reference to FIGS. 13-15, can further improve the performance of the machine. In this improvement, the machine maintains a record of the direction which it should use as the basis of forming the spike, which will be called the 'spike baseline'. This is measured as an absolute angle. The spike itself is formed at 90° to the spike baseline. Ordinarily, the spike baseline is aligned with the boundary. As the machine follows a new portion of the boundary, the machine will turn to point in a new direction, which will be called the 'wall follow direction'. As the machine turns, it monitors the angular difference (θ) between the current spike baseline direction and the new wall follow direction. Providing the difference is less than a predetermined threshold value, such as 45°, the machine continues to form spikes from the spike baseline direction. As soon as the wall follow angle exceeds the threshold angle, the machine resets the spike baseline direction to the new wall follow direction, and begins working from this new baseline. This is illustrated in FIGS. 13 and 14 and a flow diagram for the method is shown in FIG. 15.

Figure 13A:
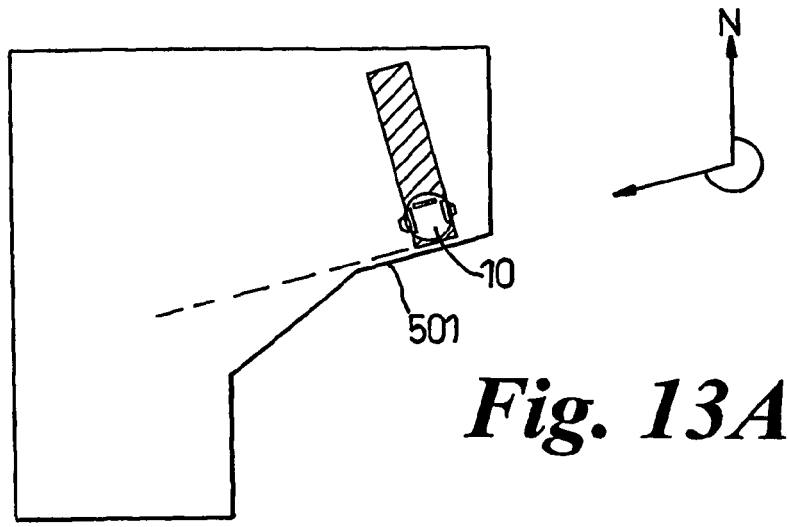
FIGS. 13A to 13C, 14A to 14C and 15 illustrate a modification to the navigation method.
Figure 13B:
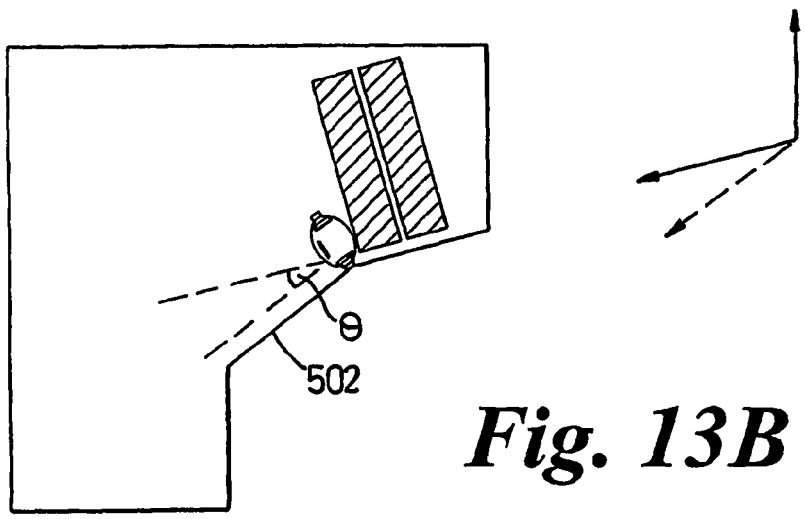
Figure 13C:
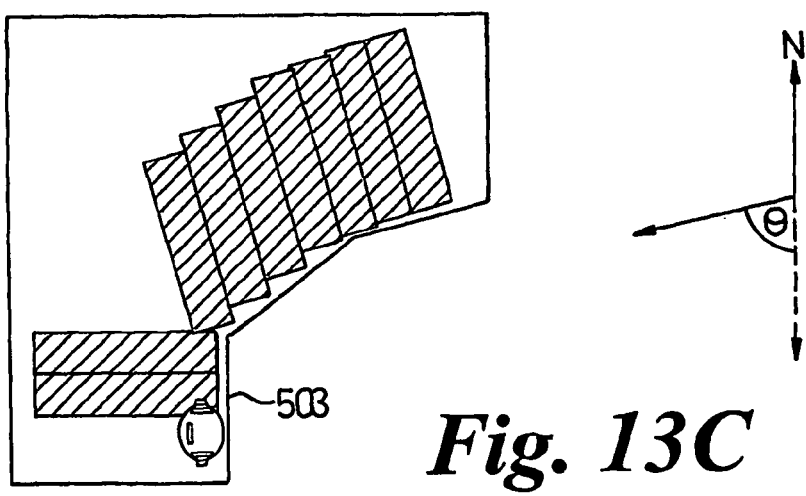

In FIG. 13A, the machine 10 is working with a spike baseline direction which is aligned with the direction of the boundary portion 501. The absolute direction of the spike baseline is shown as a bearing next to the diagram of the room. In FIG. 13B the machine 10 turns to align itself with boundary portion 502. The angular difference between the spike baseline direction and the wall follow direction is around 30°, which is less than the threshold value of 45°, and thus the machine 10 continues to form spikes from the spike baseline direction as it moves along boundary portion 502. In FIG. 13C the machine 10 has turned again to align itself with boundary portion 503. The angular difference between the spike baseline direction and the new wall follow direction is around 70° and thus the machine resets the spike baseline direction to the direction of boundary portion 503 and forms spikes from this new baseline.

Figure 14A:
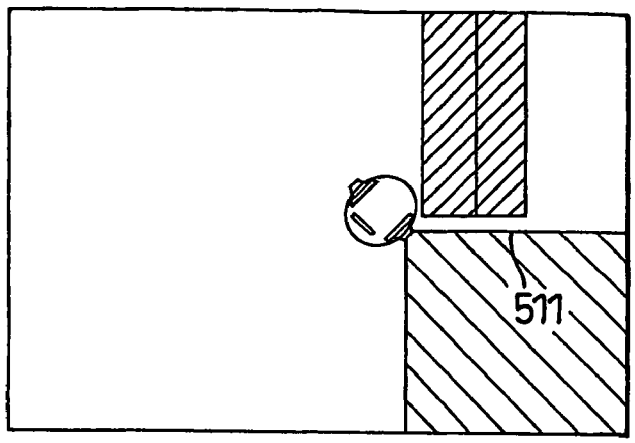
Figure 14B:
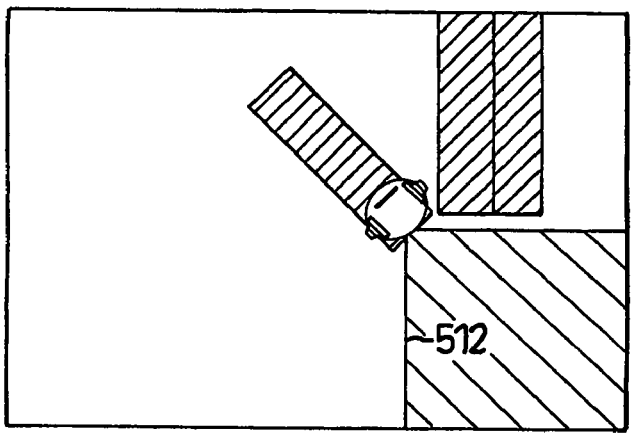
Figure 14C:
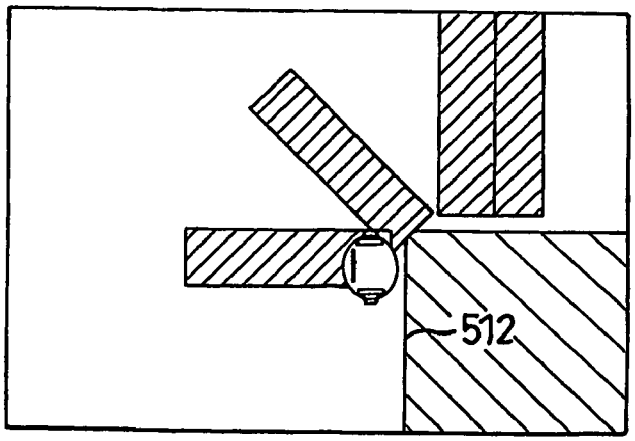
Figure 15:
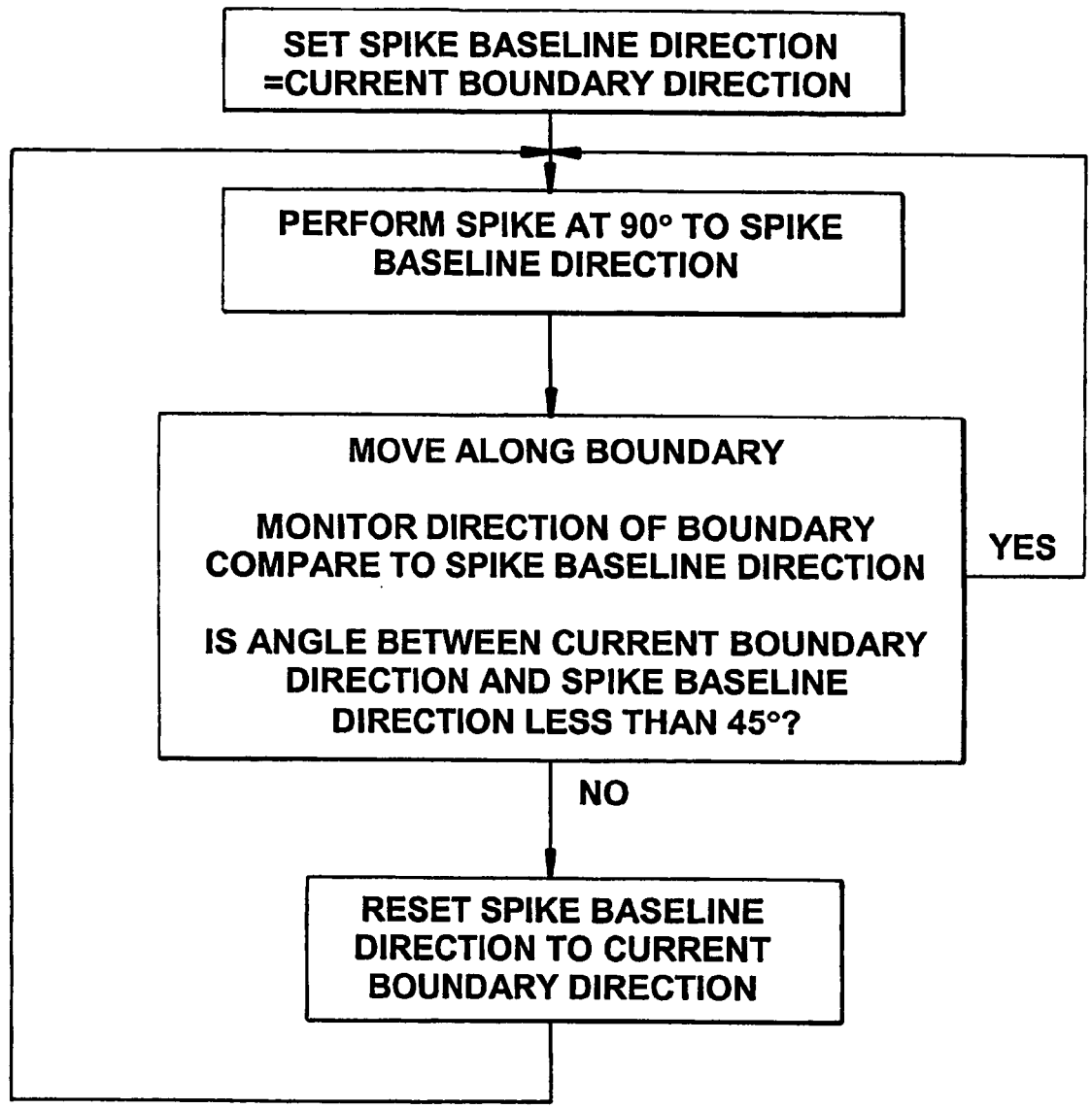

FIG. 14 shows how the machine copes with a typical 90° corner in the boundary of a working area. In FIG. 14A, the machine is working with a spike baseline aligned with the direction of boundary portion 511.

This improvement allows the machine to define a set of spike-like paths which are substantially parallel to one another, even when the boundary has an irregular shape.

In a more advanced machine the step distance between adjacent paths can be chosen by the user. There are various ways in which the user can choose the step distance: the user can be presented with a plurality of buttons or a control that specifies the step distances, or controls having symbols or descriptions indicative of the effect of the cleaner operating at the step distances, such as "normal cleaning", "thorough cleaning". The buttons can be incorporated in the user panel (60, FIG. 1), a remote control or both of these.

The invention claimed is:

1. An autonomous machine comprising:
    a control system configured to navigate the autonomous machine around an outer boundary of an enclosed working area while performing a plurality of spike movements so that the autonomous machine travels over substantially all of a free surface of the enclosed working area,
    wherein each of the plurality of spike movements comprises,
        an outward movement, away from the outer boundary of the enclosed working area,
        an inward movement, toward the outer boundary of the enclosed working area, and
        a sideways movement, substantially parallel to the outer boundary of the enclosed working area,
    wherein the control system is further configured to navigate the autonomous machine such that;
        sideways movements of the spike movements are performed around substantially all of the outer periphery of the outer boundary, and
        when the autonomous machine, when travelling along a first portion of the outer boundary and performing spike movements relative to the first portion of the outer boundary, encounters a second portion of the outer boundary that is positioned at an angle, internal to the outer boundary, of approximately 90 degrees relative to the first portion of the outer boundary, the autonomous machine is configured to begin to travel along the second portion of the outer boundary performing spike movements relative to the second portion of the boundary and substantially perpendicular to the spike movements performed relative to the first portion of the outer boundary,
    wherein when performing at least one of the spike movements relative to the second portion of the outer boundary, the autonomous machine is configured to travel over a portion of the free surface of the enclosed working area that the autonomous machine previously travelled over while performing a spike movement relative to the first portion of the outer boundary, and
    wherein the control system is further configured to return the autonomous machine to substantially a same position at which the navigation began when the autonomous machine has travelled over substantially all of a free surface of the enclosed working area.

2. An autonomous machine according to claim 1, wherein the control system is configured so that, during a spike movement, the outward movement and inward movement are along paths which are substantially the same.

3. An autonomous machine according to claim 2, wherein the control system is configured so that the machine is caused to reverse during the inward movement.

4. An autonomous machine according to claim 1, wherein the control system is configured so that, during a spike movement, the outward movement and inward movement are along paths which are adjacent to, or partially overlap, one another.

5. An autonomous machine according to claim 4, wherein the control system is configured so that the amount of overlap can be controlled by a user.

6. An autonomous machine according to claim 1, 4 or 5, wherein the control system is configured so that, during a spike movement, the outward movement is for a maximum predetermined distance.

7. An autonomous machine according to claim 1, 4 or 5, wherein the control system is configured so that the outward movement is for the shortest of the events of: (a) reaching an obstacle and (b) travelling for a predetermined distance.

8. An autonomous machine according to claim 1, 4 or 5, wherein the control system is configured so that each spike movement is at an angle which is substantially perpendicular to that part of the boundary from which it commences.

9. An autonomous machine according to claim 1, 4 or 5, wherein the control system is configured so that each spike movement is at an angle which is substantially perpendicular to a baseline direction, the baseline direction ordinarily being aligned with the outer boundary, and wherein the baseline direction is changed when the angular difference between the current baseline direction and a direction of a subsequent portion of the outer boundary is greater than a predetermined amount.

10. An autonomous machine according to claim 1, 4 or 5, wherein the control system is configured so that the outward movement of a spike movement follows a path which is adjacent to, or partially overlapping with, the return trip of the previous spike movement.

11. An autonomous machine according to claim 1, further comprising a location marker to be positioned at a starting point and a detector for detecting the location marker, and wherein the control system is arranged to recognize the starting point by detecting the location marker.

12. An autonomous machine according to claim 11, wherein the machine is powered via a power cable and the location marker is positionable on the power cable.

13. An autonomous machine according to claim 11 or 12, wherein the location marker is magnetic and the detector on the machine is responsive to the magnetic location marker.

14. An autonomous machine according to claim 11, wherein the machine is powered by an external power supply and the machine stores a length of power cable for connecting the machine to the external supply.

15. An autonomous machine according to claim 14, wherein, during each spike movement, the machine is configured to dispense the power cable during the outward movement and to rewind the power cable during the inward movement.

16. An autonomous machine according to claim 14 or 15, wherein during the inward movement the machine follows the cable which has been laid during the outward movement.

17. An autonomous machine according to claim 14 or 15, wherein during the inward movement the machine navigates to the outer boundary using odometry information.

18. An autonomous machine according to claim 14 or 15, wherein the control system is configured to cause the machine to stop following the outer boundary of the working area if the machine has dispensed all of the power cable.

19. An autonomous machine according to claim 18, wherein, if all of the power cable has been dispensed from the machine and the machine has not yet traveled over substantially all of the free space of the enclosed working area, the control system is configured to return to a starting position in the enclosed working area and to begin moving in an opposite direction around the outer boundary from the starting position.

20. An autonomous machine according to claim 19, wherein, when the machine moves around the outer boundary in the opposite direction from the starting position, the control system is configured to detect when the autonomous machine has travelled around the entire outer boundary.

21. An autonomous machine according to claim 20, wherein the control system builds a map of visited positions in the enclosed working area and is configured to recognize when it has travelled around the entire outer boundary by using the map.

22. A method of operating an autonomous machine around an enclosed working area in a manner that causes the machine to traverse substantially all of the free surface of the enclosed working area, the method comprising:
   causing the autonomous machine to navigate around an outer boundary of the enclosed working area while performing a plurality of spike movements,
   wherein each of the plurality of spike movements comprises,
      an outward movement, away from the outer boundary of the enclosed working area,
      an inward movement, toward the outer boundary of the enclosed working area, and
      a sideways movement, substantially parallel to the outer boundary of the enclosed working area,
   further causing the autonomous machine to navigate such that;
      sideways movements of the spike movements are performed around substantially all of the outer periphery of the outer boundary, and
      when the autonomous machine, when travelling along a first portion of the outer boundary and performing spike movements relative to the first portion of the outer boundary, encounters a second portion of the outer boundary that is positioned at an angle, internal to the outer boundary, of approximately 90 degrees relative to the first portion of the outer boundary, the autonomous machine is configured to begin to travel along the second portion of the outer boundary performing spike movements relative to the second portion of the boundary and substantially perpendicular to the spike movements performed relative to the first portion of the outer boundary,
   wherein when performing at least one of the spike movements relative to the second portion of the outer boundary, the autonomous machine is configured to travel over a portion of the free surface of the enclosed working area that the autonomous machine previously travelled over while performing a spike movement relative to the first portion of the outer boundary, and
   wherein the autonomous machine is further caused to return to substantially a same position at which the navigation began once the autonomous machine has travelled over substantially all of a free surface of the enclosed working area.

23. A storage medium encoded with executable instructions representing software for controlling the movement of an autonomous machine around an enclosed working area in a manner that causes the autonomous machine to traverse substantially all of the free surface of the enclosed working area,
   the software being arranged to cause the autonomous machine to navigate around an outer boundary of an enclosed working while performing a plurality of spike movements,
   wherein each of the plurality of spike movements comprises,
      an outward movement, away from the outer boundary of the enclosed working area,
      an inward movement, toward the outer boundary of the enclosed working area, and
      a sideways movement, substantially parallel to the outer boundary of the enclosed working area,
   wherein the software is further arranged to cause the autonomous machine to navigate such that;
      sideways movements of the spike movements are performed around substantially all of the outer periphery of the outer boundary, and
      when the autonomous machine, when travelling along a first portion of the outer boundary and performing spike movements relative to the first portion of the outer boundary, encounters a second portion of the outer boundary that is positioned at an angle, internal to the outer boundary, of approximately 90 degrees relative to the first portion of the outer boundary, the autonomous machine is configured to begin to travel along the second portion of the outer boundary performing spike movements relative to the second portion of the boundary and substantially perpendicular to the spike movements performed relative to the first portion of the outer boundary,
   wherein when performing at least one of the spike movements relative to the second portion of the outer boundary, software is further arranged to cause the autonomous machine to travel over a portion of the free surface of the enclosed working area that the autonomous machine previously travelled over while performing a spike movement relative to the first portion of the outer boundary, and
   wherein the software is further arranged to cause the autonomous machine to return to substantially a same position at which the navigation began when the autonomous machine has travelled over substantially all of a free surface of the enclosed working area.

* * * * *